United States Patent
Dobbs et al.

(10) Patent No.: US 7,072,039 B2
(45) Date of Patent: Jul. 4, 2006

(54) ACTIVE MULTIPLE-COLOR IMAGING POLARIMETRY

(75) Inventors: Michael E. Dobbs, Fort Wayne, IN (US); Jeff D. Pruitt, Fort Wayne, IN (US); Matthew L. Gypson, Fort Wayne, IN (US); Benjamin R. Neff, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 303 days.

(21) Appl. No.: 10/644,038

(22) Filed: Aug. 20, 2003

(65) Prior Publication Data

US 2005/0041249 A1    Feb. 24, 2005

(51) Int. Cl.
*G01J 4/00* (2006.01)

(52) U.S. Cl. ...................................... 356/364

(58) Field of Classification Search ......... 356/364–370
See application file for complete search history.

(56) References Cited

U.S. PATENT DOCUMENTS

| | | | | |
|---|---|---|---|---|
| 4,105,337 A | * | 8/1978 | Bjorklund et al. | 356/364 |
| 4,427,889 A | | 1/1984 | Muller | |
| 5,357,960 A | * | 10/1994 | Schmidtke et al. | 600/301 |
| 5,548,404 A | | 8/1996 | Kupershmidt et al. | |
| 6,144,450 A | * | 11/2000 | Jopson et al. | 356/364 |
| 6,327,037 B1 | * | 12/2001 | Chou et al. | 356/484 |
| 6,781,686 B1 | * | 8/2004 | Hunt | 356/237.2 |
| 6,927,853 B1 | * | 8/2005 | Geiler et al. | 356/367 |
| 2004/0021864 A1 | * | 2/2004 | McAlexander et al. | 356/364 |
| 2004/0227942 A1 | * | 11/2004 | Law et al. | 356/364 |

OTHER PUBLICATIONS

Gypson et al., "Polarization Imaging Using Active Illumination and Lock-In Like Algorithms", SPIE vol. 5158, 2003, pp. 161-167.
"Polarization Science and Remote Sensing", SPIE, Aug. 2003.
"Lidar Remote Sensing for Environmental Monitoring IV", SPIE, Aug. 2003.
Pruitt et al., "High-speed CW Lidar Retrieval Using Spectral Lock-in Algorithm", SPIE, vol. 5154 2003, pp. 138-145.
Dobbs et al., "Validation of Design for Space Based Tunable Diode Laser Absorption Spectroscopy Payload", SPIE, vol. 4817, 2002, pp. 123-128.
International Search Report, Int'l Appln. PCT/US2004/027009, dated Aug. 19, 2004.

* cited by examiner

Primary Examiner—Michael P. Stafira
(74) Attorney, Agent, or Firm—RatnerPrestia

(57) ABSTRACT

Remotely sensing a target may include generating a first beam of optical radiation that is modulated at a first frequency and polarized at a first polarization. A second beam of optical radiation that is modulated at a second frequency and polarized at a second polarization may also be generated. The first and second beams of optical radiation may be transmitted to the target. Radiation at the first polarization and radiation at the second polarization may be detected from the target using a phase sensitive technique and the first and second frequencies.

20 Claims, 3 Drawing Sheets

ACTIVE MULTIPLE-COLOR IMAGING POLARIMETRY

BACKGROUND OF THE INVENTION

1. Field of the Invention

This invention relates to remote sensing and, more particularly, to active remote sensing and specifically active polarimetery.

2. Description of Related Art

Active remote sensing may be conceptualized as viewing radiation reflected and/or emitted from a certain location. Active remote sensing typically utilizes one or more sources of radiation (e.g., infrared, visible, or ultraviolet light) to illuminate a target area while measuring the reflected, scattered and/or emitted radiation at one or more detectors. Where the detector(s) in a sensor produce or construct a two-dimensional image of the target that includes a number of pixels, such a sensor is typically referred to as an "imaging" sensor. Such remote sensing may be performed from a moving platform or from a stationary location, each of which may be spatially remote from the target area.

One type of remote sensor, such as a spectrometer, may detect radiation in one or more wavelength regions. Another type of remote sensor, a polarimeter, may detect radiation at one or more polarizations (which may also be referred to as "colors" to denote their different behavior even though the different polarizations may not be visually perceived in different wavelength regions). For imaging polarimeters, it is typically desirable to produce images at two or more different polarizations to enable detection of specific objects/areas within a target field of view that reflect/scatter/emit radiation differently under different polarizations.

One scheme for generating images at different polarizations is to use multiple detectors with different polarizing optics to separately image one target. In such a scheme, however, image mis-registration, where corresponding pixels in different detectors do not spatially correspond to the same location on the target, becomes troublesome. Other schemes have been proposed to use a single detector (e.g., focal plane array) and to separate the differently polarized images into, for example, quadrants or sets of adjacent pixels within the detector. These schemes, however, also suffer the mis-registration problem to some degree.

Thus, there is a need in the art to perform active polarization imaging while avoiding mis-registration among images at different polarizations.

SUMMARY OF THE INVENTION

Systems and processes consistent with the principles of the invention may extract different polarization information from a single detection signal, thereby avoiding mis-registration among images.

In accordance with one purpose of the invention as embodied and broadly described herein, a system for sensing a sample may include a first source configured to emit first optical radiation with a first polarization and that varies at a first frequency. A second source may be configured to emit second optical radiation with a second polarization and that varies at a second frequency. A detector may be configured to detect the first and second optical radiation after interaction with the sample and generate a detection signal. A first lock-in amplifier may be configured to process the detection signal based on the first frequency to produce a first output signal. A second lock-in amplifier may be configured to process the detection signal based on the second frequency to produce a second output signal.

In another implementation consistent with principles of the invention, a method of remotely sensing a sample may include transmitting a first beam of optical radiation toward the sample and transmitting a second beam of optical radiation toward the sample. The first beam may have a first polarization and an amplitude varying at a first frequency. The second beam may have a second polarization different from the first polarization and an amplitude varying at a second frequency different from the first frequency. The method may also include detecting the first and second beams of optical radiation after interaction with the sample to produce a detection signal and determining a first portion of the detection signal that is present at the first frequency. A second portion of the detection signal that is present at the second frequency may also be determined. Polarization information about the sample may be obtained based on the first portion of the detection signal and the second portion of the detection signal.

In a further implementation consistent with principles of the invention, a system for sensing a sample may include a number of sources configured to emit optical radiation. Each one of the number of sources may be configured to emit radiation at a different frequency and a different polarization from other ones of the number of sources. A single detector may be configured to detect the optical radiation from the number of sources after interaction with the sample and generate a detection signal. A number of lock-in amplifiers corresponding to the number of sources may be respectively configured to generate components of the detection signal that are present at the different frequencies. The components of the detection signal may correspond to radiation from the sample at the different polarizations.

In a yet another implementation consistent with principles of the invention, a method of remotely sensing a target may include generating a first beam of optical radiation that is modulated at a first frequency and polarized at a first polarization. The method may also include generating a second beam of optical radiation that is modulated at a second frequency and polarized at a second polarization. The first and second beams of optical radiation may be transmitted to the target. Radiation at the first polarization and radiation at the second polarization may be detected from the target using, for example, a phase sensitive technique and the first and second frequencies.

BRIEF DESCRIPTION OF THE DRAWINGS

The accompanying drawings, which are incorporated in and constitute a part of this specification, illustrate an embodiment of the invention and, together with the description, explain the invention. In the drawings.

DETAILED DESCRIPTION

The following detailed description of the invention refers to the accompanying drawings. The same reference numbers may be used in different drawings to identify the same or similar elements. Also, the following detailed description does not limit the invention. Instead, the scope of the invention is defined by the appended claims and equivalents.

As described herein, in one implementation consistent with the principles of the invention, a remote sensing system may modulate radiation at different frequencies and polarize the radiation with different polarizations before interaction with a sample of interest. A number of lock-in amplifiers may be used to process radiation detected from the sample to obtain information at the different polarizations from the sample.

EXEMPLARY SYSTEM

Figure 1:
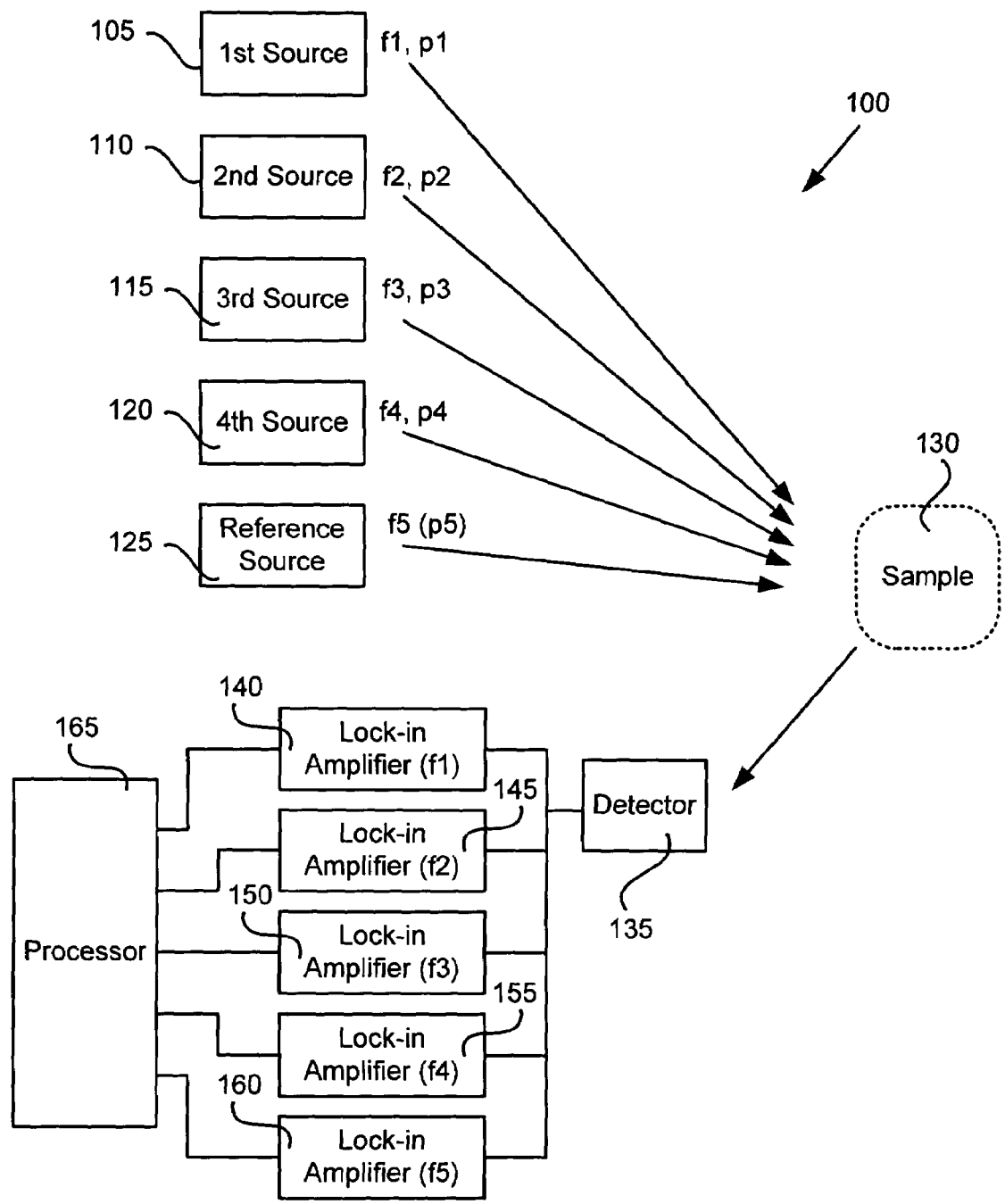
FIG. 1 is a schematic diagram of an active remote sensing system according to an implementation consistent with the principles of the invention.

FIG. 1 is a schematic diagram of an exemplary active remote sensing system 100 according to an implementation consistent with the principles of the invention. System 100 may include first through fourth sources 105/110/115/120, a reference source 125, a sample 130, a detector 135, first through fifth lock-in amplifiers 140/145/150/155/160, and a processor 165.

Each one of sources 105/110/115/120/125 may include a source of optical or other radiation that is modulated at a different characteristic frequency f1/f2/f3/f4/f5. In one implementation consistent with the principles of the invention, the outputs of at least sources 105/110/115/120 may also be differently-polarized with four different (i.e., first through fourth, respectively) polarizations p1/p2/p3/p4. Reference source 125 may also be polarized differently from sources 105/110/115/120 (i.e., with a fifth polarization p5), or reference source 125 may not be polarized. In one implementation consistent with the principles of the invention, the wavelengths of radiation produced by sources 105/110/115/120/125 may be about the same; in other implementations, wavelengths may vary among sources 105/110/115/120/125 and/or in time.

Figure 2:
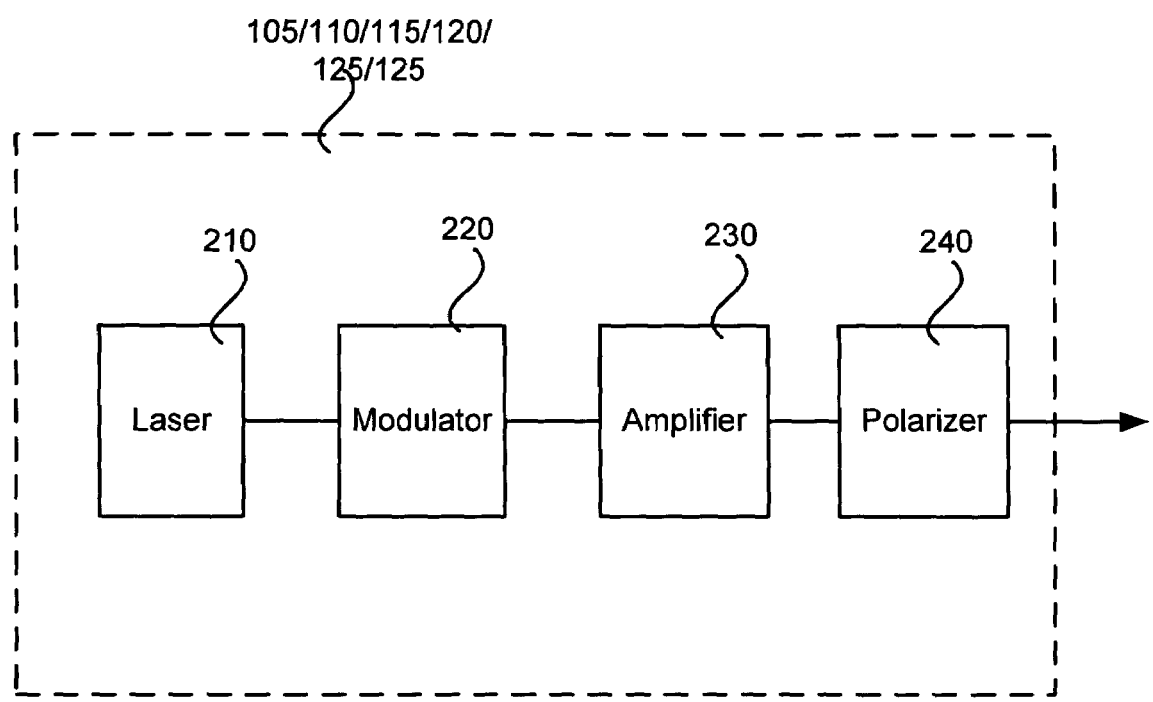
FIG. 2 illustrates an exemplary implementation of a source in the remote sensing system of FIG. 1.

FIG. 2 is an exemplary implementation of one or more of sources 105/110/115/120/125. Sources 105/110/115/120/125 may include a laser 210, a modulator 220, an optional amplifier 230, and a polarizer 240.

Laser 210 may include, for example, a distributed feedback (DFB) laser that is precisely tunable in wavelength via a combination of temperature and current. Examples of such lasers 210 include gas, solid, diode, and other types of lasers, such as fiber lasers. Laser 210 may alternately or additionally include a diode laser or an amplified diode laser. The wavelengths of the emitted radiation may fall in the ultraviolet, visible, short-wavelength infrared (SWIR), mid-wavelength infrared (MWIR), long-wavelength infrared (LWIR), or any other electromagnetic region suitable for active remote sensing. Optics (not shown) may be configured to direct the emitted radiation to modulator 220.

Modulator 220 may include an electro-optic (EO) modulator that is configured to impart a modulation (e.g., at a first modulation frequency f1 for first source 105) to the output signal from laser 210. In one implementation consistent with the principles of the invention, modulator 220 may impart an amplitude modulation to the output signal from laser 210. One exemplary modulation frequency (e.g., frequency f1) may be about 5 kHz, although this is merely an example and other first modulation frequencies f1 may be employed. In one implementation consistent with the principles of the invention, the second through fourth modulation frequencies f2/f3/f4 of second through fourth sources 110/115/120 may be different from (and perhaps also not a harmonic of) the first modulation frequency f1 of first source 105. It may be possible to introduce certain modulation frequencies in laser 210. In such cases, modulator 220 may not be a separate component, but may instead be included in laser 210 and may directly impart a desired modulation on laser 210.

Amplifier 230 may be optionally used after modulator 220. If present, amplifier 230 may be configured to amplify the radiation from modulator 220. In one implementation consistent with the principles of the invention, amplifier 230 may include an erbium-doped fiber amplifier (EDFA) or similar optical amplifier. Although not shown, amplifier 230 may also include one or more of amplifier control circuitry and a beam expander. Those skilled in the art will recognize that various combinations of optical components may be used within amplifier 230 (and/or laser 210 and modulator 220) to achieve desired properties of the emitted radiation.

Polarizer 240 may include optics (either fixed or adjustable) to impart a known polarization to the radiation at its input. In one implementation consistent with the principles of the invention, polarizer 240 may be a polarizing optical filter that only allows light of a certain polarization to pass through. As one example, polarizers 240 for first through fourth sources 105/110/115/120 may respectively impart polarizations p1 through p4 of S (i.e., sigma- or saggital plane polarized), P (i.e., pi- or tangential plane polarized), RC (i.e., right-hand circularly polarized), and LC (i.e., left-hand circularly polarized). Alternatively, polarization may be imparted by a polarization maintaining fiber laser.

In some implementations consistent with the principles of the invention, reference source 125 may be arranged similarly to first through fourth sources 105/110/115/120 shown in FIG. 2. In such cases, reference source 125 may be differently polarized (and possibly randomly polarized) from first through fourth sources 105/110/115/120. In other implementations, reference source 125 may not be polarized, in which case it may not include polarizer 240.

Those skilled in the art will appreciate that other configurations of components may be used in first through fourth sources 105/110/115/120 (and reference source 125). For example, it may be possible to introduce certain modulation frequencies in laser 210. In such cases, modulator 220 may not be a separate component, but may instead be included in laser 210. Also, sources 105/110/115/120 may use a common amplifier 230 having four outputs, instead of four different amplifiers 230.

Returning to FIG. 1, first through fourth sources 105/110/115/120 and reference source 125 may include optics (not shown) to direct their respectively polarized radiation toward the same field of view (FOV). That is, radiation from first through fourth sources 105/110/115/120 and reference source 125 may be separately transmitted, but may overlap in the far field at sample 130.

Sample 130 may include a material to be examined by laser polarimetry. In one implementation, sample 130 may include a cell in, for example, a laboratory environment. In other implementations, sample 130 may include a volume of the atmosphere, which may or may not have a scattering background (e.g., the ground, for a down-looking system 100). Sample 130 may include a solid surface (e.g., the ground), objects (e.g., vehicles), vegetation, chemicals, gas/aerosol, or any other typical target of active remote sensing that has spectral features capable of spectral measurement.

Sample 130 may contain a substance having at least one spectral feature that interacts with differently-polarized light in different manners. For example, light of one polarization may be mostly reflected, but light of another polarization may be mostly absorbed. As another example, vegetation may have a similar reflectance/emittance among different polarizations, but man-made materials (e.g., paint, fabrics, metals in vehicles, etc.) may behave differently among different polarizations.

Detector 135 may detect optical radiation reflected from or transmitted through sample 130. In one implementation consistent with the principles of the invention, detector 130 may include a multi-pixel, focal plane array (FPA) that generates an image of a portion of sample 130 from multiple detector elements therein. Optics (not shown) may assist in forming an image onto detector 135. Detector 135 may be configured to convert received optical energy into an electrical signal, such as a digital signal. Detector 135 may include a high speed (i.e., high bandwidth) photodiodes and/or signal conditioning circuitry such as analog-to-digital converters (ADCs) that digitize the electrical signal.

Detector 135 may output an electrical detection signal. Although referred to as a single detection signal, the output of detector 135 may in fact be a series of signals generated by multiple, pixel-type, individual elements within detector 135. Such signals may be output in parallel (e.g., by row or column), and/or may be time-multiplexed into a single detection signal as will be understood by one skilled in the remote imaging arts. Because the detection signal is generated after interaction with sample 130, it may yield one or more spectral (e.g., polarization) characteristics of sample 130 when processed, as will be described in greater detail below.

First lock-in amplifier 140 may be configured to receive the detection signal from detector 135 and perform, for example, "phase-sensitive" detection (or another detection technique) upon the detection signal at an operational frequency f1. The operational frequency f1 of first lock-in amplifier 140 may be selected to be the same as the modulation frequency f1 of first source 105. Those skilled in the electrical arts will be familiar with the operation and construction of lock-in amplifiers (e.g., including tuned filters, mixers, phase shifters, and low pass filters, or similar functions in a digital signal processor (DSP)). In one implementation consistent with the principles of the invention, first lock-in amplifier 140 may operate on a digital detection signal from detector 135 via an internal DSP, and may be configured to receive an external reference signal at frequency f1 (not shown) from first source 105 or processor 165.

As those skilled in the art will appreciate, the operational frequency f1 of first lock-in amplifier 140 and first source 105 may be selected high enough to significantly reduce 1/f noise that may be present in the radiation emitted by first source 105. It will be appreciated that the noise may be imparted by laser 210, detector 135, and the atmosphere. First lock-in amplifier 140 may output a first signal to processor 165 that corresponds to a portion of the detection signal from detector 135 that is present at frequency f1. Because the output of first source 105, in addition to being modulated at frequency f1, may be polarized at a first polarization p1 (e.g., S-polarized), the first signal from first lock-in amplifier 140 also corresponds to the portion of the detection signal from detector 135 (e.g., signal power) that is present at the first polarization p1. In this manner, the signal from first source 105 with first polarization p1 may be discerned from, for example, a pixel of detector 135 whose output also includes signals from second through fourth sources 110–120 and reference source 125. By using a lock-in amplifier, such as first lock-in amplifier 140, for remote sensing, background and atmospheric noise may be significantly reduced.

Second lock-in amplifier 145 may be configured to receive the detection signal from detector 135 and perform, for example, "phase-sensitive" detection (or other detection techniques) upon the detection signal at an operational frequency f2. The operational frequency f2 of second lock-in amplifier 145 may be selected to be the same as the modulation frequency f2 of second source 110. In one implementation consistent with the principles of the invention, second lock-in amplifier 145 may operate on a digital detection signal from detector 135 via an internal DSP, and may be configured to receive an external reference signal at frequency f2 (not shown) from second source 110 or processor 165.

Second lock-in amplifier 145 may output a second signal to processor 165 that corresponds to a portion of the detection signal present at the frequency f2. Because the output of second source 110, in addition to being modulated at frequency f2, may be polarized at a second polarization p2 (e.g., P-polarized), the second signal from second lock-in amplifier 145 also corresponds to the portion of the detection signal from detector 135 (e.g., signal power) that is present at the second polarization p2. In this manner, the signal from second source 110 with second polarization p2 may be discerned from, for example, a pixel of detector 135 whose output also includes signals from first, third, and fourth sources 105, 115, and 120 and reference source 125.

Third lock-in amplifier 150, fourth lock-in amplifier 155, and fifth lock-in amplifier 160 may be configured similar to first lock-in amplifier 140 and second lock-in amplifier 145. Third lock-in amplifier 150 may output a third signal to processor 165 that corresponds to a portion of the detection signal output by detector 135 that is present at the third frequency f3 (and hence the third polarization p3) from third source 115. Fourth lock-in amplifier 155 may output a fourth signal to processor 165 that corresponds to a portion of the detection signal output by detector 135 that is present at the modulation frequency f4 (and hence the fourth polarization p4) from fourth source 120. Fifth lock-in amplifier 160 may output a fifth signal to processor 165 that corresponds to a portion of the detection signal output by detector 135 that is present at the modulation frequency f5 from reference source 125 (and the fifth polarization p5 if the output of reference source 125 is polarized).

Because the output signals from sources 105/110/115/120/125 may be modulated at frequencies f1/f2/f3/f4/f5, first through fifth lock-in amplifiers 140/145/150/155/160 permit recovery of these output signals (as modified by interaction with sample 130) from a single detection signal. Because the output signals from at least first through fourth sources 105/110/115/120 may have first through fourth polarizations p1/p2/p3/p4 respectively, four "colored" (i.e., differently polarized) images may be obtained from the same detector array 135. Because the four colors are obtained from the same portions of detector 135 (e.g., pixels), any image mis-registration is avoided by system 100.

Processor 165 may include circuitry to read, format, and/or store data from lock-in amplifiers 140/145/150/155/160. In one implementation consistent with the principles of the invention, processor 165 stores all data read from lock-in amplifiers 140/145/150/155/160 for retrieval and processing at a later date. Processor 165 may include one or more shift registers and/or other storage elements in such an implementation.

In other implementations, processor 165 may process the data from lock-in amplifiers 140/145/150/155/160, rather than merely storing "raw" data. For example, processor 165 may combine the first though fifth signals from lock-in amplifiers 140/145/150/155/160 to obtain the four images at different polarization "colors," as will be described in greater detail below. In other implementations, processor 165 may include a communication link (e.g., a wireless communication link) for transferring raw or processed data from lock-in amplifiers 140/145/150/155/160 to a remote location.

Processor 165 may also be configured to control the first through fifth modulation frequencies f1–f5 of sources 105–125, and processor 165 also may provide external reference signals at these frequencies f1–f5 to first and fifth lock-in amplifiers 140/145/150/155/160. Similarly, if polarizers 240 are adjustable, processor 165 may be configured to control the first through fourth polarizations p1–p4 of sources 105–120 and the fifth polarization p5 of reference source 125 if it is polarized.

Because the output signal from reference source 125 and the output signals from sources 105–120 may experience aspects of system 100 (e.g., atmosphere) and sample 130 equally, such common behavior among the signals enables "common mode" rejection of undesired signal perturbations. For example, processor 165 may be configured to compute the ratios of the four signals from first and fourth lock-in amplifiers 140/145/150/155 to the "power reference" signal from fifth lock-in amplifier 160. This "rationing/power monitoring" using reference source 125 (or similar techniques known to those skilled in the art) may be used to eliminate unwanted fluctuations/effects (i.e., noise) from system 100 and/or the atmosphere in later processing.

It should be noted that although FIG. 1 illustrates a five-source system 100, a smaller or larger number of sources (and lock-in amplifiers) may be used. For example, as few as two sources (e.g., first source 105 and second source 110) may be used to obtain two-color polarization images. Such sources may be used with reference source 125, or without reference source 125 if a power monitor is not desired. Similarly, more than four sources 105–120 may be used if a five-color (or greater) polarization image is desired. Further, different wavelengths may be used in sources 105–125, if desired, to accomplish some wavelength-specific form of rejection, such as speckle reduction.

PROCESS OF OBTAINING DATA

Figure 3:
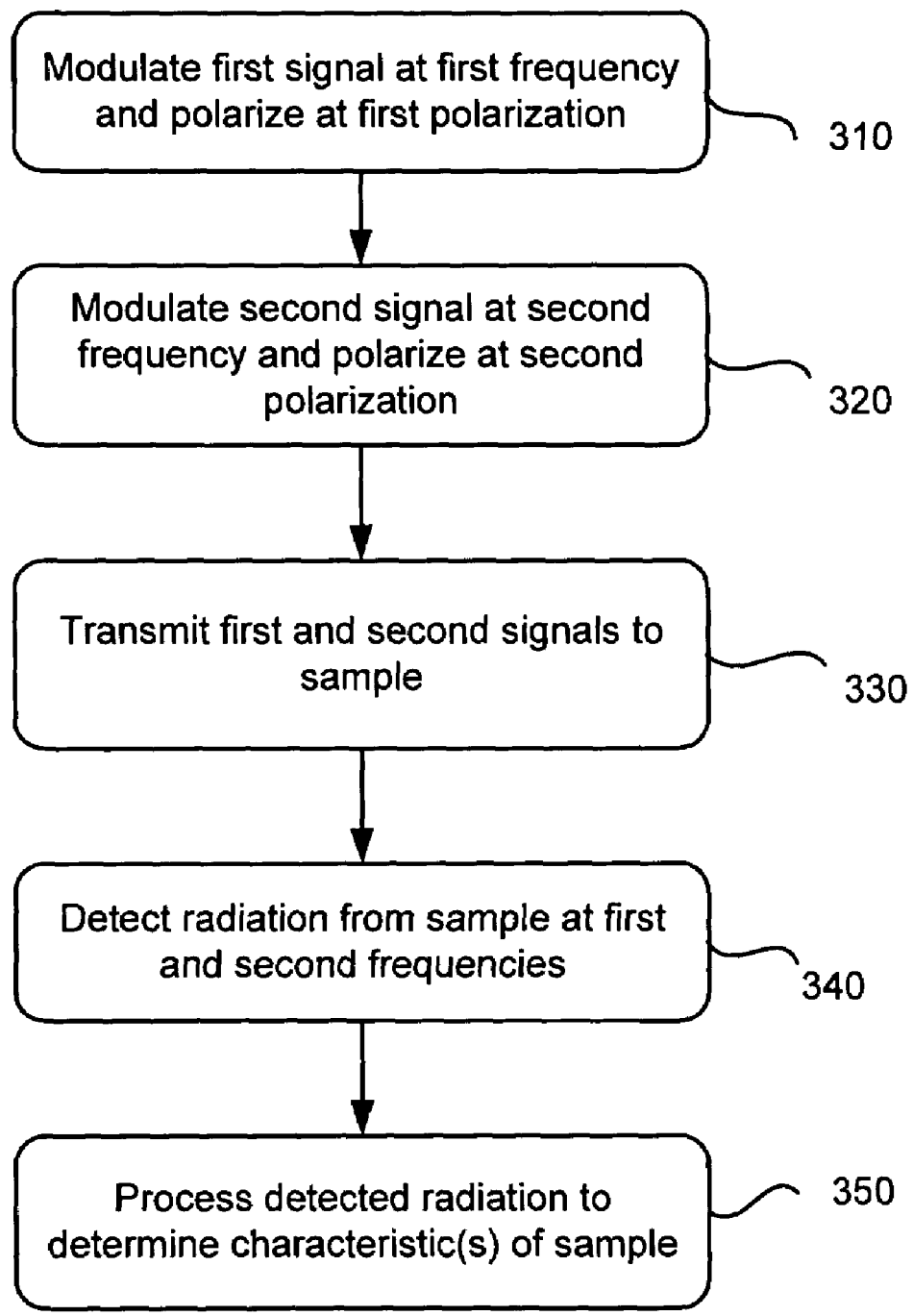
FIG. 3 is flow chart illustrating a process of actively sensing polarization information associated with a sample according to an implementation consistent with the present invention.

FIG. 3 is flow chart illustrating a process of actively sensing polarization information associated with sample 130 according to an implementation consistent with the present invention. The process may begin by modulating radiation in first source 105 at a first frequency f1 and imparting a first polarization p1 [act 310].

Second radiation from second source 110 may be modulated at a second frequency f2 that may be different from the first frequency f1 [act 320]. The radiation from second source 110 may also be polarized with a second polarization p2. Although not illustrated in FIG. 3, act 320 may optionally include generating one or more of third, fourth, and fifth radiation by sources 115, 120, and 125 that are respectively modulated at different frequencies f3/f4/f5 and have different polarizations p3/p4/p5.

Processing may continue by transmitting the first and second radiation from first source 105 and second source 110 to sample 130 [act 330]. In one implementation consistent with the principles of the invention, the first and second radiation may be transmitted separately to an overlapping field of view including at least a portion of sample 130. Sample 130 may, or may not, interact with the first radiation (at polarization p1) different from the second radiation (at polarization p2). Both the first and second radiation from sources 105 and 110 may remain modulated at their respective modulation frequencies f1 and f2 after interacting with sample 130. Although not illustrated in FIG. 3, act 330 may optionally include transmitting one or more of third, fourth, and fifth radiation from sources 115, 120, and 125 to sample 130.

Processing may continue with first and second lock-in amplifiers 140/145, in conjunction with detector 135, respectively detecting radiation from sample 130 at the first frequency f1 and the second frequency f2 [act 340]. Thus, first lock-in amplifier 140 may extract information at frequency f1 that represents signal power from sample 130 at polarization p1. Second lock-in amplifier 145 may extract information at frequency f2 that represents signal power from sample 130 at polarization p2. In one implementation consistent with the principles of the invention, detector 135 may provide information to first and second lock-in amplifiers 140/145 for a number of pixels in an array, thereby imaging sample 135.

Although not illustrated in FIG. 3, act 330 may optionally include detecting radiation at one or more of frequencies f3/f4/f5 by one or more of lock-in amplifiers 150/155/160.

The detected radiation may be processed by processor 165 to determine polarization characteristics of sample 130 [act 350]. In one implementation, images of sample 130 at different polarizations may be contrasted to highlight a portion of sample 130 that behaves differently from its surroundings (e.g., a man-made material or object). In one implementation, the signals from first and second lock-in amplifiers 140/145 (and optionally third and fourth lock-in amplifiers 150/155) may be normalized by dividing by the output of fifth lock-in amplifier 160 (corresponding to reference source 125) to facilitate meaningful comparison among different polarizations.

The above-described spectral lock-in technique uses lock-in signal recovery techniques to perform multiple-color polarization sensing. This technique permits generation of different-color polarization images that are perfectly spatially registered, because the data used to generate such images comes from the same elements in detector 135.

CONCLUSION

Systems and methods consistent with the principles of the invention may modulate radiation at different frequencies and polarize the radiation with different polarizations before interaction with a sample of interest. A number of lock-in devices may be used to process radiation detected from the sample to obtain information at the different polarizations from the sample.

The foregoing description of preferred embodiments of the present invention provides illustration and description, but is not intended to be exhaustive or to limit the invention to the precise form disclosed. Modifications and variations are possible in light of the above teachings or may be acquired from practice of the invention.

For example, the phase sensitive detection technique described herein may be used in multiple sensing scenarios. It may be used to: probe areas or materials for concentrations of certain chemicals; determine the presence of harmful chemicals in civilian areas; monitor environmental processes; monitor industrial processes; monitor industrial environments; find and track chemicals in air/water; provide early warning of threats; and/or any other detection scenario that those skilled in the art may envision involving one or more spectral features of interest.

Moreover, the acts in FIG. 3 need not be implemented in the order shown; nor do all of the acts need to be performed. Also, those acts that are not dependent on other acts may be performed in parallel with the other acts. Further, the acts in these figures may be implemented as instructions, or groups of instructions, in a computer-readable medium.

No element, act, or instruction used in the description of the present application should be construed as critical or essential to the invention unless explicitly described as such. Also, as used herein, the article "a" is intended to include one or more items. Where only one item is intended, the term "one" or similar language is used. The scope of the invention is defined by the claims and their equivalents.

What is claimed:

1. A system for remotely imaging a sample, using optical radiation reflected/scattered from the sample, comprising:
    a first source configured to emit first optical radiation with a first polarization and that varies at a first frequency;
    a second source configured to emit second optical radiation with a second polarization and that varies at a second frequency;
    a focal planar array (FPA) configured to detect the first and second optical radiation after interaction with the sample and generate a single detection signal;
    a first lock-in amplifier configured to process the single detection signal based on the first frequency to produce a first output signal; and
    a second lock-in amplifier configured to process the single detection signal based on the second frequency to produce a second output signal,
    wherein the FPA detects the first and second optical radiation free-of image mis-registration.

2. The system of claim 1, wherein the first source includes:
    a laser configured to emit radiation,
    a modulator configured to modulate the radiation at the first frequency, and
    a polarizer configured to impart the first polarization to the radiation.

3. The system of claim 1, wherein the second source includes:
    a laser configured to emit radiation,
    a modulator configured to modulate the radiation at the second frequency, and
    a polarizer configured to impart the second polarization to the radiation.

4. The system of claim 1, further comprising:
    a third source configured to emit third optical radiation with a third polarization and that varies at a third frequency; and
    a third lock-in amplifier configured to process the detection signal based on the third frequency to produce a third output signal.

5. The system of claim 1, further comprising:
    a processor configured to process the first output signal and the second output signal to obtain polarization information relating to the sample.

6. The system of claim 5, further comprising:
    a reference source configured to emit optical radiation that varies at a reference frequency; and
    a reference lock-in amplifier configured to process the detection signal based on the reference frequency to produce a reference output signal,
    wherein the processor is configured to divide the first output signal and the second output signal by the reference output signal.

7. A method of remotely imaging a sample, using optical radiation reflected/scattered from the sample, comprising:
    transmitting a first beam of optical radiation toward the sample, the first beam having a first polarization and an amplitude varying at a first frequency;
    transmitting a second beam of optical radiation toward the sample, the second beam having a second polarization different from the first polarization and an amplitude varying at a second frequency different from the first frequency;
    detecting, using a FPA, the first and second beams of optical radiation after interaction with the sample to produce a detection signal, wherein the first and second beams of optical radiation are detected by the FPA free-of image mis-registration;
    determining a first portion of the detection signal that is present at the first frequency;
    determining a second portion of the detection signal that is present at the second frequency; and
    obtaining polarization information about the sample based on the first portion of the detection signal and the second portion of the detection signal.

8. The method of claim 7, further comprising:
    generating first optical radiation;
    modulating the first optical radiation at the first frequency to obtain modulated radiation; and
    polarizing the modulated radiation to obtain the first beam of optical radiation.

9. The method of claim 8, further comprising:
    amplifying the modulated radiation before the polarizing.

10. The method of claim 7, wherein the determining a first portion of the detection signal uses a lock-in technique and a reference signal at the first frequency, and
    wherein the determining a second portion of the detection signal uses the lock-in technique and the reference signal at the second frequency.

11. The method of claim 7, wherein the polarization information about the sample includes optical power from the sample at the first polarization and optical power from the sample at the second polarization.

12. A system for remotely imaging a sample, using optical radiation reflected/scattered from the sample, comprising:
    a plurality of sources configured to emit optical radiation, each one of the plurality of sources being configured to emit radiation at a different frequency and a different polarization from other ones of the plurality of sources;
    a single FPA configured to detect the optical radiation from the plurality of sources after interaction with the sample and generate a detection signal wherein the plurality of sources are detected by the FPA free-of image mis-registration; and
    a plurality of lock-in amplifiers corresponding to the plurality of sources and respectively configured to generate components of the detection signal that are present at the different frequencies,
    wherein the components of the detection signal correspond to radiation from the sample at the different polarizations.

13. The system of claim 12, wherein the plurality of sources includes at least four sources, and
    wherein the plurality of lock-in amplifiers includes at least four corresponding lock-in amplifies.

14. The system of claim 12, wherein the components of the detection signal include a plurality of images at the different polarizations.

15. The system of claim 12, further comprising:
a reference source configured to emit unpolarized optical radiation at a reference frequency that is different from the different frequencies of the plurality of sources; and
a reference lock-in amplifier configured to generate a reference component of the detection signal that is present at the reference frequency.

16. The system of claim 15, further comprising:
a processor configured to normalize the components of the detection signal that are present at the different frequencies based on the reference component of the detection signal that is present at the reference frequency.

17. A method of remotely imaging a target using optical radiation reflected/scattered from the target, comprising:
generating a first beam of optical radiation that is modulated at a first frequency and polarized at a first polarization;
generating a second beam of optical radiation that is modulated at a second frequency and polarized at a second polarization;
transmitting the first and second beams of optical radiation to the target; and
detecting, free-of image mis-registration on an FPA, radiation at the first polarization and radiation at the second polarization from the target using a phase sensitive technique and the first and second frequencies.

18. The method of claim 17, wherein the detecting includes:
converting optical radiation into an electrical detection signal,
performing the phase sensitive technique on the electrical detection signal using the first frequency to detect the radiation at the first polarization, and
performing the phase sensitive technique on the electrical detection signal using the second frequency to detect the radiation at the second polarization.

19. The method of claim 17, wherein the generating a first beam includes:
emitting first optical radiation;
modulating the first optical radiation at the first frequency to obtain modulated radiation; and
polarizing the modulated radiation at the first polarization to obtain the first beam of optical radiation.

20. The method of claim 17, wherein the generating a second beam includes:
emitting second optical radiation;
modulating the second optical radiation at the second frequency to obtain modulated radiation; and
polarizing the modulated radiation at the second polarization to obtain the second beam of optical radiation.

* * * * *